United States Patent [19]

Frechet et al.

[11] Patent Number: 5,635,571
[45] Date of Patent: Jun. 3, 1997

[54] POLYMERIZABLE MACROMONOMERS AND POLYMERS PREPARED THEREFROM

[75] Inventors: Jean M. J. Frechet, Ithaca, N.Y.; Koji Yui, Wakayama, Japan

[73] Assignee: Cornell Research Foundation, Inc., Ithaca, N.Y.

[21] Appl. No.: 660,684

[22] Filed: Jun. 5, 1996

Related U.S. Application Data

[62] Division of Ser. No. 491,350, Jun. 30, 1995, abandoned.

[51] Int. Cl.$^6$ .................... C08L 79/04; C08G 73/06
[52] U.S. Cl. .................... 525/410; 525/417; 528/367; 528/403; 528/424; 548/237; 548/239; 560/103; 560/105; 560/110; 560/251; 560/266
[58] Field of Search .................... 525/410, 417; 528/367, 403, 424; 548/237, 239; 560/103, 105, 110, 251, 266

[56] References Cited

U.S. PATENT DOCUMENTS

| | | | |
|---|---|---|---|
| 3,483,145 | 12/1969 | Levy et al. | 548/237 |
| 4,540,747 | 9/1985 | Saegusa et al. | 528/403 |
| 4,857,630 | 8/1989 | Kim | 528/397 |
| 5,041,516 | 8/1991 | Frechet et al. | 528/44 |
| 5,136,014 | 8/1992 | Figuly | 528/272 |
| 5,196,502 | 3/1993 | Turner et al. | 528/272 |
| 5,214,122 | 5/1993 | Turner et al. | 528/272 |
| 5,225,522 | 7/1993 | Turner et al. | 528/361 |

OTHER PUBLICATIONS

Chemical Abstracts 101:231861, "Thermally Stable Polyesters" Jun. 1984.
Chemical Abstracts 115:135986, "Synthesis of 2-Functionally Substituted Oxazolines" 1991.
Structure Diagrams for Chemical Abstracts Registry Nos. 29257-50-9; 17612-21-4; 10826-66-4; 16105-42-3 and 131269-11-9.
Levy, A., et al., J. Polym. Sci., Part A-1, vol. 6, No. 7, pp. 1883–1894 (1968).
Alper, J., Science, 251, 1562–1564 (Mar. 1991).
Futuretech Strategic Markets, No. 161, Technical Insights, Inc., Engelwood, NJ, pp. 1–20, May 24, 1993.
Hawker, C.J., et al, J. Am. Chem. Soc. 114, 8405–8413 (1992).
Hawker, C. J., et al, J. Chem. Soc. Perkin Trans. 1, 2459–2469 (1992).
High–Tech Materials Alert, vol. 10, No. 5, pp. 1–2, May 1993.
Hodge, P., Nature, 362, 18–19, Mar. 4, 1993.
Gitsov, I., et al, Angew. Chem. Int. Ed. Engl., 31, No. 9, 1200–1202, 1992.
Hawker, C., et al. J. Chem. Soc., Chemical Communications, Issue 15, 1990, pp. 1010–1013.
Hawker, C. J., et al, Polymer, 33, 1507–1511 (1992).
Hawker, C. J., et al, Chemistry in Australia, 620–622, Dec. 1992.
Inside R & D, p. 5, Apr. 21, 1993.
Saville, P. M., et al, J. Phys. Chem., 97, 293–294, 1993.
Hawker, C. J., et al, J. Am. Chem. Soc. 112, 7638–7647 (1990).
Hawker, C. J., et al, Polymer Prep. 34(1), 54–55 (1993).

*Primary Examiner*—Frederick Krass

[57] ABSTRACT

Polyoxazolines having the structural formula:

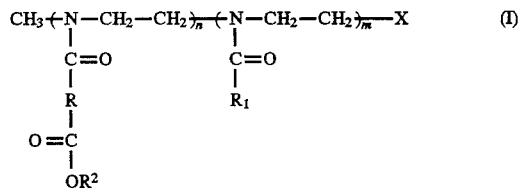

wherein R is phenylene or alkylene containing 2 to 18 carbon atoms, $R^2$ is $C_{1-4}$ alkyl and $R_1$ is selected from the group consisting of $C_{1-12}$ alkyl, vinyl, isopropylidene, pentafluoroethyl, phenyl, hydroxyphenyl which is optionally interrupted by up to 20 ethylene oxide groups, $C_{1-2}$-alkoxyphenyl which is optionally interrupted by up to 20 ethylene oxide groups and $-(CH_2CH_2-O-)_rCH_3$ in which r ranges from 1–20, X is $NH_2$ or OH, n ranges from 2 to 50 and m ranges from 0 to 50, wherein $R_1$ is hydroxyphenyl optionally interrupted by up to 20 ethylene oxide groups only when X is $NH_2$, are polymerizable to form hyperbranched polymers which have a number average molecular weight ranging from 5,000 to 150,000, a weight average molecular weight ranging from 5,500 to 5,000,000 and a polydispersity ranging from 1.1 to 300 and which are very polar and highly wettable and are useful as adhesives, biodegradable materials, biomaterials, carriers for chemicals, carriers for image contrast agents, coatings, components of blends, components of medical imaging formulations, crosslinkers, dispersants, drug carriers, imaging materials, resists for lighography, slow release agents, vectors for gene therapy, and viscosity modifiers.

10 Claims, 1 Drawing Sheet

POLYMERIZABLE MACROMONOMERS AND POLYMERS PREPARED THEREFROM

This application is a division, of application Ser. No. 08/491,350, filed Jun. 30,1995, now abandoned.

TECHNICAL FIELD

This invention is directed to a novel method of preparing hyperbranched polymers, to novel $AB_x$-type compounds useful in said method and to hyperbranched polymers prepared from said $AB_x$-type compounds by said method.

BACKGROUND OF THE INVENTION

Interest in hyperbranched polymers dates back to the early fifties with the publication of a theoretical paper by Flory, J. Am. Chem. Soc., 74, 2719 (1952) which states "Highly branched polymer molecules may be synthesized without the incidence of gelation through the use of monomers having one functional group of one kind and two or more of another capable of reacting with the former."

Since that time, there has been a good deal of activity involving condensation polymerization of $AB_x$ monomers where A and B functions condense together to obtain highly branched polymers.

However, obtaining high molecular weights has involved multi-step procedures.

SUMMARY OF THE INVENTION

The invention herein involves the novel concept of polymerizing $AB_x$ macromonomers instead of low molecular weight $AB_x$ monomers similar to those that have previously been used and the obtaining of $AB_x$ macromonomers which can be polymerized to obtain highly branched polymers of high molecular weights.

One embodiment of the invention herein is directed to a process of preparing a hyperbranched polymer comprising polymerizing an $AB_x$ macromonomer wherein A is $NH_2$ or OH group resulting from a termination step in preparing the macromonomer and B is pendant ester group present in monomer used to prepare said macromonomer. When A is $NH_2$ group, the reaction involved in producing the hyperbranched polymer is amidation between pendant ester group B of macromonomer and chain terminating $NH_2$ group A of macromonomer so that resulting polymer molecule has a single $NH_2$ terminated chain, and the polymerization is carried out under amidation conditions. When A is OH group, the reaction involved in producing the hyperbranched polymer is transesterification between pendant ester group B of macromonomer and chain terminating OH group A of macromonomer so that each resulting polymer molecule has a single OH terminated chain and the polymerization is carried out under transesterification conditions.

Another embodiment of the invention herein is directed to macromonomers which are polyoxazolines having the structural formula:

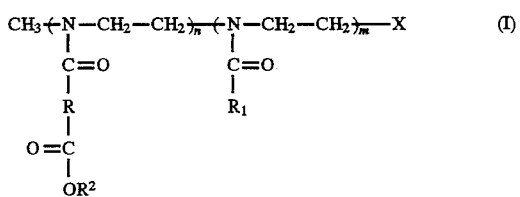

wherein R is phenylene or alkylene containing 2 to 18 carbon atoms, $R^2$ is $C_{1-4}$ alkyl, $R_1$ is selected from the group consisting of $C_{1-12}$ alkyl, vinyl, isopropylidene, pentafluoroethyl, phenyl, hydroxyphenyl which is optionally interrupted by up to 20 ethylene oxide groups, $C_{1-2}$-alkoxyphenyl which is optionally interrupted by up to 20 ethylene oxide groups and $-(CH_2CH_2-O-)_rCH_3$ in which r ranges from 1–20, X is $NH_2$ or OH, n ranges from 2 to 50, and m ranges from 0 to 50, wherein $R_1$ is hydroxyphenyl which is optionally interrupted by up to 20 ethylene oxide groups only when X is $NH_2$. In these polyoxazolines X is the A group and the pendant ester groups are the x B groups for the $AB_x$ structure. In the polyoxazoline macromonomers where m is not 0, the resulting copolymers can be block copolymers or non block copolymers, e.g., random copolymers, and the structure (I) is meant to represent this.

Still another embodiment of the invention herein is directed to hyperbranched polymers obtained by polymerizing said polyoxazoline macromonomers, which hyperbranched polymers have a number average molecular weight ranging from 5,000 to 150,000, a weight average molecular weight ranging from 5,500 to 5,000,000 and a polydispersity ranging from 1.1 to 300.

The polyoxazolines macromonomers herein are thus useful to produce the hyperbranched polymers herein by the method herein.

The hyperbranched polymers herein are very polar and highly wettable and are useful as coatings, adhesives, viscosity modifiers, crosslinkers, biomaterials, components of blends, drug carriers, vectors for gene therapy, carriers for agrochemicals such as antifungal agents, slow release agents, biodegradable materials, imaging materials, resists for lithography, carriers for image contrast agents, components of medical imaging formulations and dispersants. The hyperbranched polymers herein prepared from macromonomers herein where m is not 0 and $R_1$ is pentafluoroethyl, have low surface energy and can be used to prepare non-stick, soil release and antistain surfaces. The hyperbranched polymers herein have the advantage of being easily producible from macromonomers which are easily synthesized and designed using oxazoline chemistry.

The term "macromonomer" is used herein to mean oligomer or polymer molecule that has reactive groups allowing it to be used in a subsequent polymerization reaction. The polyoxazolines (I) are oligomers or polymers containing repeating units containing functional groups.

The term "hyperbranched" is used herein to mean highly branched.

The number average molecular weights herein and the weight average molecular weights herein are determined by size exclusion chromatography calibrated by polyethylene oxide standard using N-methyl-2-pyrrolidinone as mobile phase. The polydispersity is determined by dividing the weight average molecular weight by the number average molecular weight. Number average molecular weight is sometimes referred to herein as Mn. Weight average molecular weight is sometimes referred to herein as Mw. Polydispersity is sometimes referred to herein as PD.

DETAILED DESCRIPTION OF THE INVENTION

Figure 1:
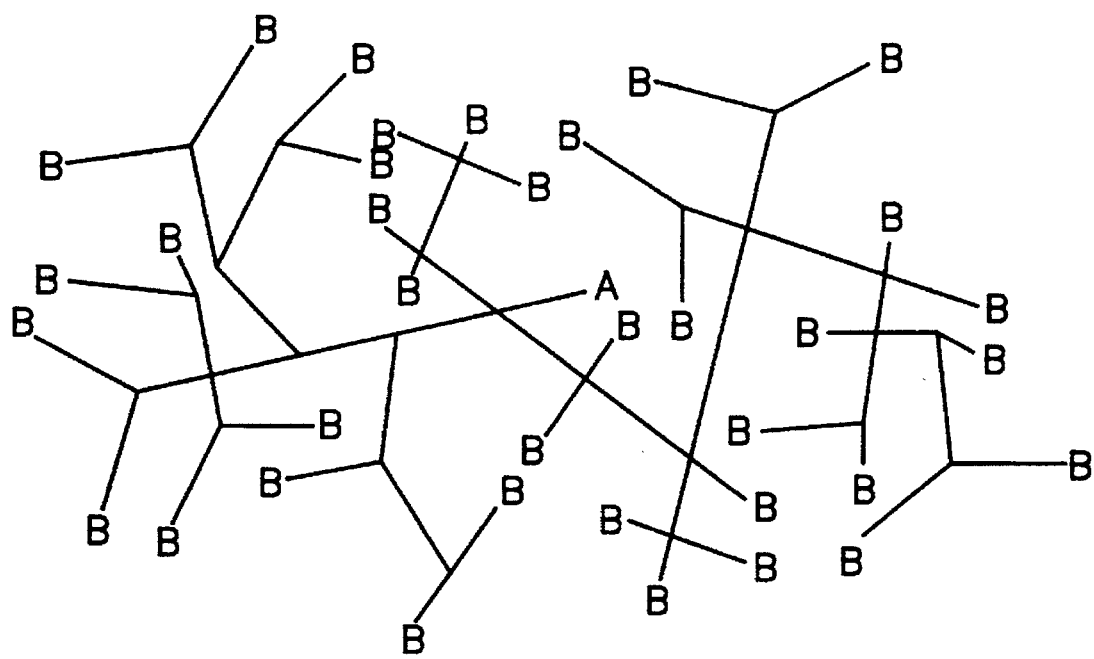
FIG. 1 is a schematic representation of hyperbranched polymer herein.

We turn firstly to polyoxazaline macromonomers herein having the structural formula (I) wherein R is phenylene, $R^2$ is $C_{1-4}$ alkyl (including methyl, ethyl, propyl, and butyl), X is $NH_2$, n ranges from 2 to 50 and m is 0. In one subgenus, n ranges from 4 to 25.

The macromonomers described in the above paragraph are prepared starting with an oxazoline monomer with an ester pendant group and reacting to cause a ring-opening cationic polymerization followed by chain termination using ammonia and neutralization to obtain the amino ($NH_2$) end group.

We turn now to said oxazoline monomer with an ester pendant group. This is 2-(3- or 4-$C_{1-4}$-alkoxycarbonyl) phenyl-2-oxazoline which has the following structure:

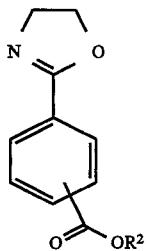

wherein $R^2$ is $C_{1-4}$ alkyl. The monomer 2-(4-methoxycarbonyl)phenyl-2-oxazoline can be prepared from commercially available materials as described in Example I hereinafter. The monomer 2-(3-methoxy)phenyl-2-oxazoline can be prepared as described in Example I hereinafter when 3-methoxycarbonylbenzoyl chloride is substituted for 4-methoxycarbonylbenzoyl chloride. The monomer 2-(4-ethoxycarbonyl)phenyl-2-oxazoline can be prepared as described in Example I hereinafter when 4-ethoxycarbonylbenzoyl chloride is substituted for 4-methoxycarbonylbenzoyl chloride. The monomer 2-(3-ethoxycarbonyl)phenyl-2-oxazoline can be prepared as described in Example I hereinafter when 3-ethoxycarbonylbenzoyl chloride is substituted for 4-methoxycarbonylbenzoyl chloride. The 3- and 4-propoxy and 3- and 4-butoxy compounds can be prepared in similar fashion starting with the corresponding 3- and 4-alkoxycarbonyl benzoyl chlorides.

Said oxazoline monomer can be subjected to the ring opening cationic polymerization (the term "cationic polymerization" is used because the growing end of the macromonomer involves cationically charged structure) by admixing with a minimally nucleophilic solvent of the type normally used in the cationic polymerization of oxazoline derivatives and then reacting in the presence of an initiator at a reaction temperature in the range of 60°–120° C., for example, in the range from 105°–115° C., for 1 to 72 hours.

The minimally nucleophilic solvents include, for example, saturated aliphatic nitriles, such as acetonitrile; saturated aliphatic esters, such as ethyl acetate; saturated aliphatic ethers, such as tetrahydrofuran; saturated aliphatic chlorinated hydrocarbons, such as chloroform and 1,2-dichloroethane; and chlorinated benzenes, such as chlorobenzene. Acetonitrile is the preferred reaction solvent.

The initiators include, for example, electrophilic alkylating or benzylating agents, such as alkyl or benzyl trifluoromethane sulfonate, alkyl or benzyl trifluoroacetate, alkyl or benzyl sulfate, alkyl or benzyl p-toluenesulfonate, and alkyl or benzyl methanesulfonate. The alkyl is preferably lower alkyl, i.e., $C_1$–$C_4$ alkyl. The preferred initiator is methyl trifluoromethanesulfonate.

Because water can terminate this kind of cationic polymerization, moisture should be removed as much as possible and the reaction is preferably carried out in a sealed reactor. Cooling prior to sealing of the reactor will prevent evaporation of the reaction solvent and of the initiator.

The chain termination providing $NH_2$ at the terminal end is readily carried out by reacting with ammonia to cause the terminal cationic group to become a primary ammonium group and then reacting with sodium hydroxide to convert the primary ammonium group to free amino group.

The reaction with ammonia is preferably carried out using ammonia in solution in a non-nucleophilic solvent. Solution of ammonia in 1,4-dioxane is commercially available. While gaseous ammonia can be used, it is not convenient to use where very small and exact amounts of ammonia are desired.

The ammonia can be utilized, for example, in an amount ranging from 1.5 to 2 times the stoichiometric amount where the stoichiometric amount is the same molar amount as that of the initiator used in the reaction.

The reaction with ammonia can be carried out at room temperature (20°–30° C.). Reaction times greater than 3 hours provide reasonably complete reaction.

Reaction with sodium hydroxide subsequent to reaction with ammonia, for example by washing with saturated sodium chloride aqueous solution containing 1% sodium hydroxide, converts the terminal primary ammonium group to free amine.

Reaction pressure is not important in this reaction. The reason why the reactor is preferably sealed is to prevent the entrance of moisture into the reaction mixture and to prevent evaporation of the solvent if the solvent boiling point is lower than the polymerization temperature. The polymerization can normally be carried out under atmospheric pressure of dry inert gas such as nitrogen or argon.

The variable that controls the degree of polymerization n is the ratio of molar amount of monomer to molar amount of initiator. The degree of polymerization n is controlled by changing the feed ratio, i.e., the ratio of molar amount of monomer to molar amount of initiator. The theoretical degree of polymerization DP=[Monomer]/[Initiator].

We turn now to polyoxazoline macromonomers herein having the structural formula (I) wherein R is alkylene containing 2 to 18 carbon atoms, e.g., 2 to 6 carbon atoms and exemplified hereinafter by alkylene containing 4 carbon atoms, $R^2$ is $C_{1-4}$ (including methyl, ethyl, propyl, butyl), X is $NH_2$, n ranges from 2 to 50 and m is 0. In one subgenus, n ranges from 4 to 25.

The macromonomer of the above paragraph can be prepared the same as the macromonomer described above where R is phenylene, X is NH$_2$ and m is 0 except that the oxazoline monomer is 2-(ω-C$_{1-4}$-alkoxy carbonylalkyl)-2-oxazoline having the structure:

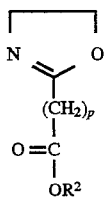

where p ranges from 2 to 18 and R$^2$ is C$_{1-4}$ alkyl. This oxazoline monomer is believed to be novel. The preparation of said oxazoline monomer where p in the above structure is 4 and R$^2$ is methyl, from commercially available materials, is described in Example III hereinafter. Monomers where R$^2$ is methyl and p is different from 4 are prepared similarly to the 2-(4-methoxycarbonylbutyl)-2-oxazoline that is prepared in Example III except that the appropriate ω-methoxycarbonylalkanoyl chloride is substituted for 4-methoxycarbonylbutanoyl chloride in said Example III, and the reaction solvent is chloroform instead of ether when p is greater than 10. The monomers where R$^2$ is ethyl, propyl or butyl are prepared the same as the monomers where R$^2$ is methyl except that corresponding ethyl, propyl or butyl ester starting materials are used in place of methyl ester starting materials. The variable that controls the degree of polymerization n is the ratio of molar amount of monomer to molar amount of initiator. The theoretical degree of polymerization DP=[Monomer]/[Initiator].

We turn now to polyoxazoline macromonomers herein having the structural formula (I) wherein R is phenylene, R$^2$ is C$_{1-4}$ alkyl, R$_1$ is as described above, X is NH$_2$, n ranges from 2 to 50 and m ranges from 1 to 50. In one subgenus, n ranges from 4 to 25 and m ranges from 4 to 25. R$_1$ can be, for example, methyl, ethyl, propyl, butyl, octyl, dodecyl, pentafluoroethyl, vinyl, isopropylidene, phenyl, 2-hydroxyphenyl, 3-hydroxyphenyl, 4-hydroxyphenyl, 3-C$_{1-2}$-alkoxyphenyl, 4-C$_{1-2}$-alkoxyphenyl or -(CH$_2$CH$_2$—O-)$_r$CH$_3$ in which r ranges from 1–20. These macromonomers are prepared the same as the polyoxazoline macromonomers having the structural formula (I) wherein R is phenylene, R$^2$ is C$_{1-4}$ alkyl, X is NH$_2$, n ranges from 2 to 50 and m is 0 except that the 2-substituted-2-oxazoline,

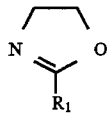

where R$_1$ is the same as described above, is added into the reaction mixture to participate in ring-opening cationic polymerization and except for such differences as described hereinafter. To form a copolymer containing a block of polymerized monomer with ester pendant group and a block of polymerized group from the 2-substituted-2-oxazoline, the 2-substituted-2-oxazoline is added and polymerized after the oxazoline monomer with pendant ester group is polymerized and before chain termination with ammonia is carried out. This polymerization to form a block of polymerized group from the 2-substituted-2-oxazoline may be carried out in the presence of initiator as described above by maintaining the reaction mixture at 60° to 120° C., for example, at 85° to 95° C., for 1 to 72 hours, for example, 15 to 25 hours. For random polymerization of the groups from monomer with ester pendant group and the groups from the 2-substituted-2-oxazoline, the 2-substituted-2-oxazoline is added initially to participate in ring-opening cationic polymerization concurrently with the ring-opening cationic polymerization of the monomer with ester pendant group and the ring opening cationic polymerization reaction may be carried out at a temperature in the range of 60° to 120° C. for 1 to 72 hours. Combinations of block and random copolymers can be prepared by addition of the monomers appropriately. The variable that controls the degree of polymerization n is the ratio of molar amount of 2-(3- or 4-C$_{1-4}$-alkoxycarbonyl)phenyl-2-oxazoline monomer to the molar amount of initiator; the theoretical degree of polymerization n is the molar amount of said oxazoline divided by the molar amount of the initiator. The variable that controls the degree of polymerization m is the ratio of molar amount of the 2-substituted-2-oxazoline to molar amount of initiator; the theoretical degree of polymerization is the molar amount of the 2-substituted-2-oxazoline divided by the molar amount of the initiator.

We turn now to polyoxazoline macromonomers herein having the structural formula (I) wherein R is alkylene containing 2 to 18 carbon atoms, R$^2$ is C$_{1-4}$ alkyl, R$_1$ is as described above, X is NH$_2$, n ranges from 2 to 50 and m ranges from 1 to 50. In one subgenus, n ranges from 4 to 25 and m ranges from 4 to 25. R$_1$ can be, for example, methyl, ethyl, propyl, butyl, octyl, dodecyl, pentafluoroethyl, vinyl, isopropylidene, phenyl, 2-hydroxyphenyl, 3-hydroxyphenyl, 4-hydroxyphenyl, 3-C$_{1-2}$-alkoxyphenyl, 4-C$_{1-2}$-alkoxyphenyl or -(CH$_2$CH$_2$—O-)$_r$CH$_3$ in which r ranges from 1–20. These macromonomers are prepared the same as the polyoxazoline macromonomers having the structural formula (I) wherein R is alkylene containing 2 to 18 carbon atoms, R$^2$ is C$_{1-4}$ alkyl, X is NH$_2$, n ranges from 2 to 50 and m is 0 except that the 2-substituted-2-oxazoline is added to the reaction mixture to participate in ring-opening cationic polymerization and except for differences as described below. To form a copolymer containing a block of polymerized monomer with ester pendant group and a block of polymerized group from the 2-substituted-2-oxazoline, the 2-substituted-2-oxazoline is added and polymerized after the oxazoline monomer with pendant ester group is polymerized and before chain termination with ammonia is carried out. This polymerization to form a block of polymerized group from the 2-substituted-2-oxazoline can be carried out in the presence of the initiator as described above by maintaining the reaction mixture at 60° to 120° C. for 1 to 72 hours. For random polymerization of the groups from monomer with ester pendant group and the groups from the 2-substituted-2-oxazoline, the 2-substituted-2-oxazoline is added initially to participate in ring-opening cationic polymerization concurrently with the ring-opening cationic polymerization of the monomer with ester pendant group and the ring opening cationic polymerization is carried out at a temperature ranging from 60° to 120° C. for 1 to 72 hours. Combinations of block and random copolymers can be prepared by addition of the monomers appropriately. The degree of polymerization n is varied by varying the ratio of molar amount of 2-(ωC$_{1-4}$-alkoxycarbonyl)alkyl-2-oxazoline oxazoline to molar amount of initiator. The degree of polymerization m is varied by varying the ratio of molar amount of the 2-substituted-2-oxazoline to molar amount of initiator.

The 2-substituted-2-oxazoline 2-ethyl-2-oxazoline is commercially available. Other commercially available 2-substituted-2-oxazolines that may be used to produce the macromonomers herein wherein m is not zero include, for example, 2-methyl-2-oxazoline, 2-phenyl-2-oxazoline and 2-isopropylidene-2-oxazoline. Other 2-substituted-2-oxazolines that may be used to produce the macromonomers herein where m is not zero, which are not commercially available, are readily prepared by those skilled in the art. For example, 2-hydroxyphenyl-2-oxazoline (meta and para isomers), 2-[(ω-hydroxy-polyethylene-oxy)-phenyl]-2-oxazoline (meta and para isomers), and 2-[(ω-methyl-polyethylene-oxy)-phenyl)]-2-oxazoline (meta and para isomers) can be prepared as described in Kobayashi, S., et al, Makromol Chem. 185, 441 (1989); 2-propyl-2-oxazoline and 2-butyl-2-oxazoline can be prepared as described in Kobayashi, S., et al, Macromolecules 25, 3232 (1992); and 2-vinyl-2-oxazoline and 2-isopropylidine-2-oxazoline can be prepared as described in Suzuki, M., et al, Polymer Bulletin 19, 247 (1988), and D. A. Tomalia, Japan Kokai 156866 (1977). In addition, 2-octyl-2-oxazoline can be prepared as described in Example XI. The procedure of Example XI is standard for many 2-alkyl-2-oxazolines as well as other 2-substityuted-2-oxazolines. In addition, a number of standard procedures have been patented and published by D. A. Tomalia. The procedures for preparing 2-substituted-2-oxazolines descibed in Examples I, III and XI, as well as those described in Tomalia's patents, can be used to produce a vast array of 2-substituted-2-oxazolines simply by changing the starting material.

The polyoxazoline macromonomers corresponding to those described above but with X being OH instead of $NH_2$ are prepared the same as the corresponding macromonomers with X being $NH_2$ except that chain termination is carried out using an excess of 10% aqueous NaOH in place of the ammonia or the ammonia solution added for preparation of $NH_2$ chain terminated compounds.

We turn now to the hyperbranched polymers that are formed from the polyoxazoline macromonomers herein. These are schematically represented by the structure depicted in FIG. 1. As depicted, the hyperbranched polymer contains a single A group (which is $NH_2$ when X in the structure (I) is $NH_2$ and which is OH when X in the structure (I) is OH) and numerous chain ends of unreacted ester groups B, i.e., $—COOR^2$ groups. The reactions involved in producing the hyperbranched polymers are amidation between pendant ester group of macromonomer and $NH_2$ of macromonomer when X in the structure (I) is $NH_2$ and transesterification between pendant ester group of macromonomer and chain terminating OH of macromonomer where X in the structure (I) is OH. The ester groups B in the hyperbranched polymer can be further modified, for example, to create free carboxylic acid groups by saponification or hydrolysis reaction or to create micelle structures constituting carboxylate salts by neutralizing said free carboxylic acid groups. The hyperbranched polymers herein are quite soluble in organic solvents such as chloroform, acetone, methylene chloride and N-methyl-2-pyrrolidone despite very high molecular weights indicating high polarities and wettabilities.

One hyperbranched polymer herein is that obtained by polymerizing polyoxazoline macromonomer having the structure (I) where X is $NH_2$, under amidation conditions so that each molecule has a single $NH_2$ terminated chain, said hyperbranched polymer having a number average molecular weight ranging from 5,000 to 150,000, a weight average molecular weight ranging from 5,500 to 5,000,000, for example, from 1,000,000 to 5,000,000, and a polydispersity ranging from 1.1 to 300, for example, from 20 to 300. The amidation conditions referred to can be, for example, heating polyoxazoline macromonomer at a temperature in the range of 100° C. to 155° C. and above the melting point of the macromonomer or in solution, for 15 to 100 hrs. An unexpected undesirable cross-linking reaction was found to occur at 160° C. The reaction is preferably carried out neat when the macromonomer reactant melts at a temperature at 155° C. or below. In such case, reduced pressure is necessary to remove alcohol (for example, methanol when $R^2$ is methyl and ethanol when $R^2$ is ethyl) reaction product. When the reaction is carried out in solution, the solvent is preferably a non-nucleophilic, non-electrophilic, polar solvent such as N-methyl-2-pyrrolidone, N,N-dimethylformamide, N,N-dimethylacetamide, dimethylsulfoxide, tetrahydrothiophene 1,1-dioxide or hexamethyl phosphorictriamide. When the reaction is conducted in solution, the pressure is not reduced so that the temperature is maintained and evaporation of solvent is minimized. Reaction may be detected by a significant decrease in the signal attributed to the ester group in the $^1H$ NMR spectrum. Quenching any remaining amino groups to prevent further reaction may be carried out by reacting with acetic anhydride to transform the remaining amino groups into unreactive acetamide groups. This acetylation can be carried out by heating at reflux temperature in a non-nucleophilic solvent such as chloroform or 1,2-dichloroethane for 1 to 10 hours.

One hyperbranched polymer of the type described in the above paragraph is formed by polymerizing polyoxazoline macromonomer having the structure (I) wherein R is phenylene, $R^2$ is $C_{1-4}$ alkyl, X is $NH_2$, n ranges from 2 to 50, e.g., from 4 to 25, and m is 0, under amidation conditions, and has a number average molecular weight ranging from 50,000 to 125,000, a weight average molecular weight ranging from 60,000 to 4,750,000, for example, from 2,000,000 to 4,750,000, and a polydispersity ranging from 1.2 to 75, for example, from 25 to 75. In preparing this hyperbranched polymer, the polyoxazoline macromonomer may be heated at a temperature in the range of 100° to 155° C., for example in the range of 130° to 155° C., and above the melting point of the macromonomer, or in solution, for 15 to 100 hours.

Another hyperbranched polymer of the type described in said same paragraph is formed by polymerizing polyoxazoline macromonomer having the structure (I) wherein R is alkylene containing 2 to 18 carbon atoms, e.g., 2 to 6 carbon atoms, $R^2$ is $C_{1-4}$ alkyl, X is $NH_2$, n ranges from 2 to 50, e.g., 4 to 25, and m is 0, under amidation conditions and has a number average molecular weight ranging from 5,000 to 150,000, for example, from 5,000 to 15,000, a weight average molecular weight ranging from 5,500 to 5,000,000, for example, from 1,500,000 to 2,500,000 and a polydispersity ranging from 1.1 to 300, for example, from 150 to 250. In preparing this hyperbranched polymer, the polyoxazoline macromonomer is heated at a temperature ranging from 100° to 155° C. neat under reduced pressure for 15 to 100 hours or in solution in a non-nucleophilic, non electrophilic, polar solvent as described above, at a temperature ranging from 100° to 155° C. for 15 to 100 hours.

Another hyperbranched polymer of the type described in said same paragraph is formed by polymerizing polyoxazoline macromonomer having the structure (I) wherein R is phenylene, $R^2$ is $C_{1-4}$ alkyl, $R_1$ is ethyl, X is $NH_2$, n ranges from 2 to 50, e.g., 4 to 25, and m ranges from 1 to 50, e.g., 4 to 25, under amidation conditions and is, for example, a block copolymer, and has a number average molecular weight ranging from 5,000 to 150,000, a weight average molecular weight ranging from 5,500 to 5,000,000, and a polydispersity ranging from 1.1 to 300. In preparing this hyperbranched polymer, the polyoxazoline macromonomer is heated at a temperature ranging from 100° to 155° C. neat under reduced pressure for 15 to 100 hours or in solution in nonnucleophilic, non-electrophilic polar solvent as described above at a temperature ranging from 100° to 155° C. for 15 to 100 hours.

Another hyperbranched polymer of the type described in said same paragraph is formed by polymerizing polyoxazoline macromonomer having the structure (I) wherein R is alkylene containing 2 to 18 carbon atoms, e.g., 2 to 6 carbon atoms, $R^2$ is $C_{1-4}$ alkyl, $R_1$ is ethyl, X is NH2, n ranges from 2 to 50, e.g., 4 to 25, and m ranges from 1 to 50, e.g., 4 to 25, under amidation conditions and is, for example, a random copolymer, and has a number average molecular weight ranging from 5,000 to 150,000, a weight average molecular weight ranging from 5,500 to 5,000,000 and a polydispersity ranging from 1.1 to 300. In preparing this hyperbranched polymer, the polyoxazoline macromonomer is heated at a temperature ranging from 100° to 155° C. neat under reduced pressure for 15 to 100 hours or in solution in nonnucleophilic, non-electrophilic polar solvent as described above at a temperature ranging from 100° to 155° C. for 15 to 100 hours.

Another hyperbranched polymer herein is that obtained by polymerizing polyoxazoline macromonomer having the structure (I) where X is OH, under transesterification conditions so that each molecule has a single OH terminated chain, said hyperbranched polymer having a number average molecular weight ranging from 5,000 to 150,000, a weight average molecular weight ranging from 5,500 to 5,000,000, for example, from 1,000,000 to 5,000,000, and a polydispersity ranging from 1.1 to 300, for example, from 20 to 300. The reaction is called polytransesterification and the resulting groups are new ester groups composed of the carbonyl group, which was originally in the $C_{1-4}$ alkyl ester moiety, and the alkoxy group which stems from removal of H from X. Alcohol by-product is eliminated. Since transesterification is an equilibrium reaction between the mixture of original $C_{1-4}$ alkyl ester group and original alcohol group X and the mixture of new ester group and the alcohol which is formed, reaction is carried out at a low pressure or at high temperature (e.g., 100° to 155° C.) so that the alcohol which is formed is continuously removed from the reaction system causing shifting of the equilibrium in favor of new ester group formation.

In the polymerizations of the polyoxazoline macromonomers herein to form the hyperbranched polymers, the alcohol by-product is separated.

The invention is illustrated by the following examples. For the experiments of these examples, acetonitrile was successively distilled from aluminum chloride, lithium carbonate and from calcium hydride under nitrogen; N-methylpyrrolidinone used as a reaction solvent was distilled from calcium hydride under reduced pressure of nitrogen; 4-methoxycarbonylbenzoyl chloride was prepared from 4-methoxycarbonylbenzoic acid according to the method of Osuka, A., et al, Bull. Chem. Soc. Jpn., 65, 2807–2813 (1992) and purified by vacuum distillation (bp 102° C./0.65 mm Hg); ethyleneimine was prepared according to the method of Allen, C.F.A., et al, Org. Syn. Coll., Vol 4, p. 433 (1963); and all other reagents and solvents were purchased and used without any purification.

EXAMPLE I

Synthesis of a Macromonomer 4a Having the Structure (I) Wherein R is Phenylene, $R^2$ is Methyl, X is $NH_2$, n is About 5 and m is 0

The synthesis carried out below is represented by the following reaction equations:

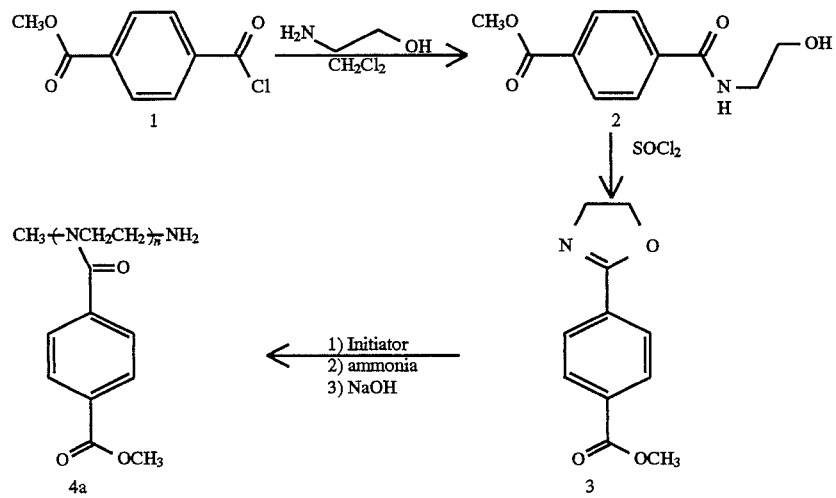

where n is about 5.

The synthesis was carried out as follows:

Into an ice-cooled and stirred solution of 4-methoxycarbonylbenzoyl chloride 1 (53.6 g, 0.270 mol) in methylene chloride was dropwisely added a solution of 2-aminoethanol (36.3 g, 0.594 mol) in methylene chloride (40 ml) under nitrogen during 1 hr, and the mixture was stirred for 3 hr at room temperature. The resulting precipitate was collected by vacuum filtration, washed thoroughly with water and dried in vacuo at 50° C. to give N-(2-hydroxyethyl)-4-methoxycarbonylbenzamide 2 (53.3 g, 88% yield) as white powder: $^1$H NMR (CD$_3$SOCD$_3$)δ3.45 (t of t, 2H, J=5.4 and 5.9 Hz, CH$_2$N), 3.64 (t, 2H, J=5.9 Hz, CH$_2$O), 3.90 (s, 3H, CH$_3$O), 4.87 (brs, 1H, OH), 8.02 (d, 2H, J=9.3 Hz, 2,6-Ar-H), 8.05 (d, 2H, J=9.3 Hz, 3,5-Ar-H), 8.65 (t, 1H, J=5.4 Hz, NH).

Into stirred thionyl chloride (22.0 g, 0.179 mol) was portionwisely added 2 (10.0 g., 0.0448 mol) at room temperature, and the mixture was stirred for additional 20 minutes. After evaporation in vacuo at room temperature, into the residual solid were carefully added chloroform and saturated sodium hydrogen carbonate aqueous solution. The mixture was shaken and separated. The chloroform layer was washed with saturated sodium hydrogen carbonate aqueous solution and brine, dried over anhydrous magnesium sulfate, and evaporated in vacuo. The resulting solid was column chromatographed on silica gel by ethyl acetate, and recrystallized from hexane-chloroform to give 2-(4-methoxycarbonyl) phenyl-2-oxazoline 3 as colorless prisms (5.72 g, 62% yield):mp 125°–127° C., $^1$H NMR (CDCl$_3$) δ3.93 (s, 3H, CH$_3$O), 4.09 (t, 2H, J=9.7 Hz, CH$_2$O), 4.46 (t, 2H, J=9.7 Hz, CH$_2$N), 8.01 (d, 2H, J=8.4 Hz, 2,6-ArH), 8.08 (d, 2H, J=8.4 Hz, 3,5-ArH) IR 3056, 2960, 2933, 2889, 2866, 1716, 1652, 1611, 1511, 1440, 1412, 1381, 1333, 1218, 1198, 1122, 1104, 1073, 1016, 972, 941, 893, 874, 840, 783, 710, 667 cm$^{-1}$. Elemental analysis: Found: C64.40, H5.43, N6.89%; calculated for C$_{11}$H$_{11}$NO$_3$: C64.38, H5.40, N6.83%.

A mixture of 3 (4.00 g, 0.0195 mol) and acetonitrile (30 ml) was placed in a dry glass reactor under nitrogen, and was cooled with ice. Into this mixture was added methyl trifluoromethane sulfonate (0.441 ml, 0.00390 mol). The reactor was sealed in vacuo, shaken thoroughly, and heated at 110° C. for 5 hr to form an intermediate A-1. After opening of the reactor at room temperature, a 0.5M solution of ammonia in 1,4-dioxane (11.7 ml, 0.00585 mol) was added into the mixture, and the resulting admixture was shaken and let stand for overnight (8–13 hr) to form a second intermediate A-2. The reaction mixture was concentrated in vacuo, dissolved in methylene chloride (70 ml), washed with saturated sodium chloride aqueous solution containing 1% sodium hydroxide (200 ml) and brine, followed by drying over anhydrous magnesium sulfate and evaporation in vacuo at room temperature to give 4a as a white powder (3.98 g, 99% yield): $^1$H NMR (CDCl$_3$)δ2.5–3.8 (br, CH$_2$), 3.94 (s, CH$_3$O), 7.1–7.6 (br, 2,6-Ar-H), 7.8–8.2 (br, 3,5-Ar-H);IR 2953, 1725, 1637, 1584, 1508, 1460, 1435, 1402, 1281, 1192, 1177, 1122, 1111, 1074, 1065, 1020, 964, 869, 827, 783, 752, 735, 729 cm$^{-1}$.

The reaction equations depicting conversion of A-1 to 4a are depicted below:

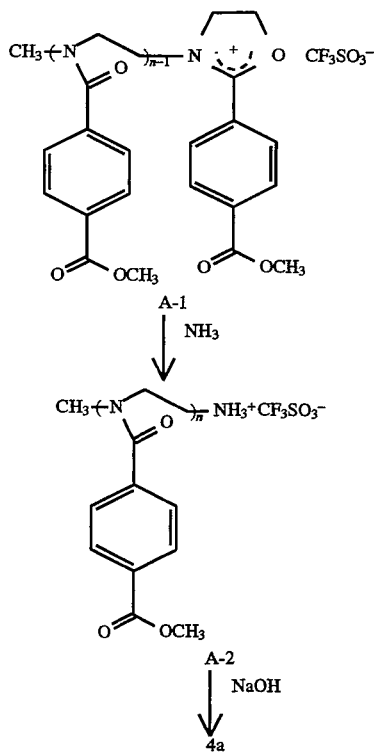

The obtained 4 a was acetylated as follows for submission to GPC analysis. The macromonomer 4a (300 mg) was mixed with acetic anhydride (310 mg, 3.0 mmol) and chloroform (5 ml), and heated at reflux under nitrogen for 3 hr. After concentration in vacuo, the residue was dissolved in methylene chloride, reprecipitated by ether, decanted, and dried in vacuo to give a white powder (200 mg, 64% yield): Mn 800, Mw 950, PD 1.19.

The compound 4a was determined to have a degree of polymerization n of about 5.

When a 10% NaOH aqueous solution (1 ml) is substituted for the solution of ammonia and appropriate purification is carried out, the macromonomer 4c obtained is essentially the same as 4a except that the chain terminating group is OH instead of NH$_2$.

EXAMPLE II

Synthesis of a Macromonomer 4b Having the Structure (I) Wherein R is Phenylene, R$^2$ is Methyl, X is N$_2$, n is about 10 and m is 0

The synthesis carried out below is represented by the same reaction equations as for Example I except that the product 4b is:

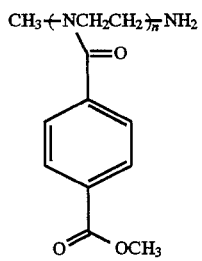

wherein n is about 10.

The synthesis was carried out as follows.

A mixture of 3 prepared as in Example I (2.00 g, 9.75 mol) and acetonitrile (19 ml) was placed in a dry glass reactor under nitrogen, and was cooled with ice. Into this mixture was added methyl trifluoromethane sulfonate (0.110 ml, 0.975 mmol). The reactor was sealed in vacuo, shaken thoroughly, and heated at 110° C. for 16 hr. After opening of the reactor at room temperature, a 0.5M solution of ammonia in 1,4-dioxane (2.90 ml, 1.45 mmol) was added into the mixture, and the resulting admixture was shaken and let stand overnight. The reaction mixture was concentrated in vacuo, dissolved in methylene chloride (40 ml), washed with saturated sodium chloride aqueous solution containing 1% sodium hydroxide (100 ml) and brine, followed by drying over anhydrous magnesium sulfate and evaporation in vacuo at room temperature to give 4b as a white powder (1.89 g, 91% yield): $^1$H NMR (CDCl$_3$)δ2.5–3.8 (br, CH$_2$), 3.8–4.0 (br, CH$_3$O), 7.0–7.6 (br, 2,6-Ar-H), 7.8–8.2 (br, 3,5-Ar-H): IR 2953, 1724, 1635, 1508, 1460, 1435, 1411, 1280, 1200, 1181, 1133, 1111, 1019, 868, 783, 747 cm$^{-1}$.

The obtained 4b was acetylated as follows for submission to GPC analysis. The macromonomer 4b (300 mg) was mixed with acetic anhydride (150 mg, 1.5 mmol) and chloroform (5 ml), and heated at reflux under nitrogen for 3 hr. After concentration in vacuo, the residue was dissolved in methylene chloride, reprecipitated by ether, decanted, and dried in vacuo to give a white powder (220 mg, 73% yield): Mn 1000, Mw 1250, PD 1.25.

The compound 4b was determined to have a degree of polymerization n of about 10.

When a 10% NaOH aqueous solution (1 ml) is substituted for the solution of ammonia and appropriate purification is carried out the macromonomer 4d obtained is essentially the same as 4b except that the chain terminating group is OH instead of NH$_2$.

EXAMPLE III

Synthesis of a Macromonomer 7 Having the Structure (I) Wherein R is Alkylene Having 4 Carbon Atoms, R$^2$ is Methyl, X is NH$_2$, n is about 20 and m is 0

The synthesis carried out below is represented by the following reaction equations:

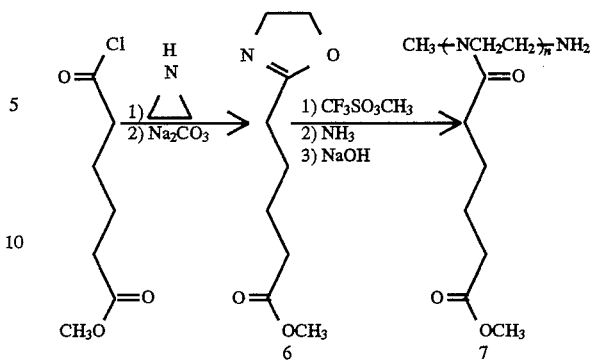

The synthesis was carried out as follows:

2-(4-Methoxycarbonylbutyl)-2-oxazoline 6 was prepared by a method similar to that disclosed in Levy, A., J. Poly. Sci., Part A-1,6, 1883–1894 (1968). This preparation was carried out as follows:

Into a solution of 4-methoxycarbonylbutanoyl chloride (30.0 g, 0.168 mol) in ether (85 ml) was added a solution of ethyleneimine (7.96 g, 0.185 mol) in ether (60 ml) dropwisely to maintain gentle reflux under nitrogen, and stirred for additional 30 minutes. The mixture was chilled in a dry ice-acetone bath, and the resulting precipitate was collected by vacuum filtration, washed with ether and dried in vacuo. The obtained solid was mixed with sodium carbonate (15 g) in a distillation flask and heated at 125° C. in vacuo (0.6 mm Hg), and a colorless liquid resulted. The liquid was distilled from calcium hydride in vacuo to give 6 as colorless liquid (10.6 g, 34% yield): bp 102° C./0.6 mm Hg; IR 2956, 2888, 1736, 1670, 1459, 1439, 1369, 1244, 1200, 1178, 1091, 1078, 991, 955, 922 cm$^{-1}$; $^1$H NMR (CDCl$_3$) δ1.6–1.8 (m, 4H, CH$_2$C=O, CH$_2$C=N), 2.25–2.5 (m, 4H, CH$_2$CH$_2$), 3.66 (s, 3H, CH$_3$O), 3.82 (t, 2H, J=9.5 Hz, CH$_2$N), 4.23 (t, 2H, J=9.5 Hz, CH$_2$O).

A mixture of 6 (2.408 g, 13.0 mmol) and acetonitrile (9.2 ml) was placed in a dry glass reactor under nitrogen, and was cooled with ice. Into this mixture was added methyl trifluoromethane sulfonate (0.0736 ml, 0.650 mmol). The reactor was sealed in vacuo, shaken thoroughly, and heated at 100° C. for 4 hr. After opening of the reactor at room temperature, a 0.5M solution of ammonia in 1,4-dioxane (2.6 ml, 1.3 mmol) was added into the mixture, and the resulting admixture was shaken and let stand overnight. The reaction mixture was concentrated in vacuo, dissolved in methylene chloride (50 ml), washed with saturated sodium chloride aqueous solution containing 1% sodium hydroxide (100 ml) and brine, followed by drying over anhydrous magnesium sulfate and evaporation in vacuo at room temperature to give 7 as a colorless paste (2.35 g, 98% yield): $^1$H NMR (CDCl$_3$)δ1.65 (brs, CH$_2$), 2.35 (brs, CH$_2$CO), 3.3–4.0 (brm, CH$_2$N), 3.65 (s, CH$_3$O); IR 3000, 2950, 1793, 1734, 1646, 1559, 1540, 1482, 1456, 1394, 1366,1269, 1241, 1173, 1147, 1087, 1055, 994, 960, 880, 770, 714 cm$^{-1}$.

The obtained 7 was acetylated as follows for submission to GPC analysis. The macromonomer 7 (220 mg) was mixed with acetic anhydride (250 mg, 1.5 mmol) and chloroform (5 ml), and heated at reflux under nitrogen for 3 hr. After concentration in vacuo, the residue was dissolved in methylene chloride, reprecipitated by ether, decanted, and dried in vacuo to give a white powder (143 mg, 65% yield); Mn 2110, Mw 2490, PD 1.18.

The compound 7 was determined to have a degree of polymerization n of about 20.

When a 10% NaOH aqueous solution (1 ml) is substituted for the solution of ammonia and appropriate purification is carried out, the macromonomer 13 obtained is essentially the same as 7 except that the chain terminating group is OH instead of $NH_2$.

EXAMPLE IV

Synthesis of a Block Copolymer Macromonomer 9 Having the Structure (I) Wherein R is Phenylene, $R^2$ is Methyl, X is $NH_2$, n is About 10 and m is About 10

The synthesis carried out below is represented by the following reaction equations:

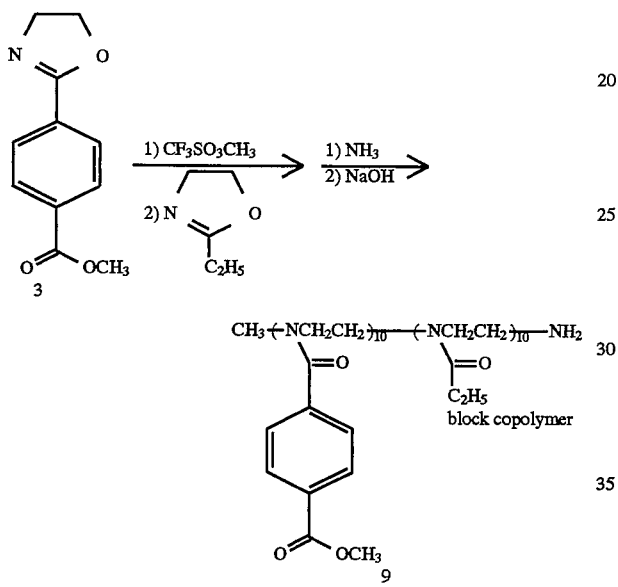

The synthesis was carried out as follows:

A mixture of 3 (2.00 g, 9.75 mmol) prepared as in Example I and acetonitrile (19 ml) was placed in a dry glass reactor under nitrogen, and was cooled with ice. Into this mixture was added methyl trifluoromethane sulfonate (0.110 ml, 0.975 mmol). The reactor was sealed in vacuo, shaken thoroughly, and heated at 110° C. for 16 hr. After opening of the reactor at room temperature, into the mixture was added 2-ethyl-2-oxazoline (0.967 g, 9.75 mmol), and the reactor was sealed again in vacuo, shaken thoroughly, and heated at 90° C. for 19 hr. Into the opened reactor was added a 0.5 M solution of ammonia in 1,4-dioxane (2.90 ml, 1.45 mMol) at room temperature, and the resulting admixture was shaken and let stand overnight. The reaction mixture was concentrated in vacuo, dissolved in methylene chloride (50 ml), washed with saturated sodium chloride aqueous solution containing 1% sodium hydroxide (100 ml) and brine, followed by drying over anhydrous magnesium sulfate and evaporation in vacuo at room temperature to give 9 as a white powder (2.67 g, 90% yield).

The compound 9 was determined to have a degree of polymerization n of about 10 and a degree of polymerization m of about 10.

When a 10% NaOH aqueous solution (1 ml) is substituted for the solution of ammonia and appropriate purification is carried out the macromonomer 14 obtained is essentially the same as 9 except that the chain terminating group is OH instead of $NH_2$.

EXAMPLE V

Synthesis of a Random Copolymer Macromonomer 11 Having the Structure (I) Wherein R is Alkylene Containing Four Carbon Atoms, $R^2$ is Methyl, X is $NH_2$, n is About 10 and m is About 10

The synthesis carried out below is represented by the following reaction equation:

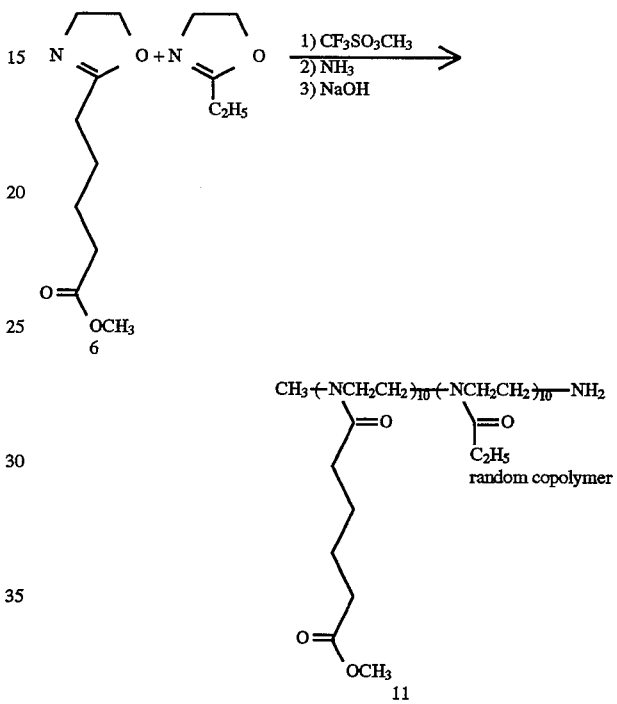

The synthesis was carried out as follows:

A mixture of 6 (2.00 g, 10.8 mmol), prepared as in Example III, 2-ethyl-2-oxazoline (1.07 g, 10.8 mmol) and acetonitrile (19 ml) was placed in a dry glass reactor under nitrogen, and was cooled with ice. Into this mixture was added methyl trifluoromethane sulfonate (0,122 ml, 1.08 mmol). The reactor was sealed in vacuo, shaken thoroughly, and heated at 90° C. for 15 hr. After opening of the reactor at room temperature, a 0.5M solution of ammonia in 1,4-dioxane (3.24 ml, 1.62 mmol) was added into the mixture, and the resulting admixture was shaken and let stand overnight. The reaction mixture was concentrated in vacuo, dissolved in methylene chloride (40 ml), washed with saturated sodium chloride aqueous solution containing 1% sodium hydroxide (100 ml) and brine, followed by drying over anhydrous magnesium sulfate and evaporation in vacuo at room temperature to give 11 as a white powder (2.86 g, 93% yield).

The compound 11 was determined to have a degree of polymerization n of about 10 and a degree of polymerization m of about 10.

When a 10% NaOH aqueous solution (1 ml) is substituted for the solution of ammonia and appropriate purification is carried out the macromonomer 15 obtained is essentially the same as 11 except that the chain terminating group is OH instead of $NH_2$.

EXAMPLE VI

Preparation of the Hyperbranched Polymer 5a from the Macromonomer 4a

The synthesis carried out below is represented by the following reaction equation:

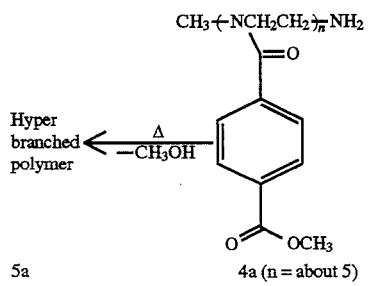

Macromonomer 4a (500 mg) prepared as in Example I was heated at 135°–140° C. under reduced pressure (0.4 mm Hg) for 22 hr. the melting point was observed at around 110° C. After cooling down to room temperature, a pale orange brittle solid was obtained (458 mg). The obtained solid was mixed with acetic anhydride (380 mg, 3.7 mmol) and chloroform (5 ml), and heated at reflux under nitrogen for 3 hr. After concentration in vacuo, the residue was dissolved in methylene chloride, reprecipitated by ether, decanted, and dried in vacuo to give a white powder (438 mg, ca 83% yield). This powder was dissolved in methylene chloride (10 ml), reprecipitated by ethyl acetate (100 ml), decanted, and dried in vacuo to give 5a as a white powder (294 mg, ca 61% yield): Mn 71,600, Mw 2,700,000, PD 37.7.

When macromonomer 4c is substituted for 4a, the hyperbranched polymer 16 obtained is essentially the same as 4a but contains OH as the chain terminating group (A in the figure) instead of $NH_2$.

EXAMPLE VII

Preparation of the Hyperbranched Polymer 5b from the Macromonomer 4b

The synthesis carried out below is represented by the following reaction equation:

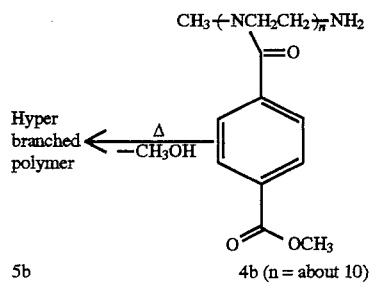

A mixture of macromonomer 4b (215 mg) prepared as described in Example II and N-methyl-2-pyrrolidinone (0.30 ml) was heated at 135°–140° C. under nitrogen for 48 hr. Into the resulting solution were added acetic anhydride (0.30 g, 0.0029 mol) and chloroform, and the resultant admixture was heated at reflux under nitrogen for 3 hr. After concentration in vacuo, the residue was dissolved in methylene chloride, reprecipitated by ether, decanted, and dried in vacuo to give a white powder (187 mg). This powder was dissolved in methylene chloride (6 ml), reprecipitated by ethyl acetate (60 ml), decanted, and dried in vacuo to give 5b as a white powder (46 mg, ca 22% yield): Mn 96,500, Mw 4,420,000, PD 45.8.

When macromonomer 4d is substituted for 4a the hyperbranched polymer 17 obtained is essentially the same as 5b but contains OH as the chain terminating group (A in the figure) instead of $NH_2$.

EXAMPLE VIII

Preparation of the Hyperbranched Polymer 8 from the Macromonomer 7

The synthesis carried out below is represented by the following reaction equation:

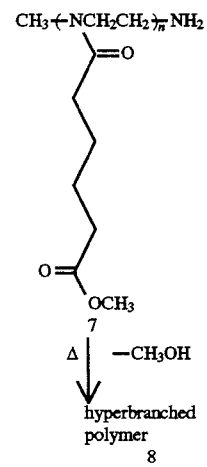

Macromonomer 7 (500 mg) prepared as in Example III was heated at 115°–120° C. under reduced pressure (0.5 mm Hg) for 45 hr. After cooling down to room temperature, a pale orange brittle solid was obtained (441 mg). The obtained solid was mixed with acetic anhydride (350 mg, 3.5 mmol) and chloroform (5 ml), and heated at reflux under nitrogen for 3 hr. After concentration in vacuo, the residue was dissolved in methylene chloride, reprecipitated by ether, decanted, and dried in vacuo to give 8 as an off-white powder (391 mg, ca 80% yield): Mn 8260, Mw 1,960,000, PD 237.

When macromonomer 13 is substituted for 8, the hyperbranched polymer 18 obtained is essentially the same as 8 but contains OH as the chain terminating group (A in the figure) instead of $NH_2$.

EXAMPLE IX

Preparation of the Hyperbranched Polymer 10 from the Macromonomer 9

The synthesis carried out below is represented by the following reaction equation:

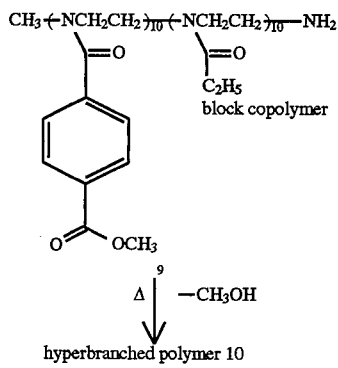

Macromonomer 9 (600 mg) prepared as in Example IV was heated at 135°–140° C. under reduced pressure (0.4 mm Hg) for 33 hr. After cooling down to room temperature, a pale orange brittle solid was obtained (572 mg). The obtained solid was mixed with acetic anhydride (400 mg, 3.92 mmol) and chloroform (7 ml), and heated at reflux under nitrogen for 3 hr. After concentration in vacuo, the residue was dissolved in methylene chloride, reprecipitated by ether, decanted, and dried in vacuo to give 10 as an off-white powder (541 mg, ca 90% yield).

When macromonomer 14 is substituted for 10, the hyperbranched polymer 19 obtained is essentially the same as 10 but contains OH as the chain terminating group (A in the figure) instead of $NH_2$.

EXAMPLE X

Preparation of the Hyperbranched Polymer 12 from the Macromonomer 11

The synthesis carried out below is represented by the following reaction equation:

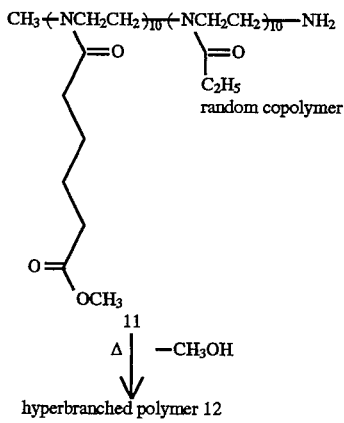

Macromonomer 11 (800 mg) prepared as in Example V was heated at 115°–120° C. under reduced pressure (0.4 mm Hg) for 45 hr. After cooling down to room temperature, a pale orange brittle solid was obtained (766 mg). the obtained solid was mixed with acetic anhydride (600 mg, 5.88mmol) and chloroform (10 ml), and heated at reflux under nitrogen for 3 hr. After concentration in vacuo, the residue was dissolved in methylene chloride, reprecipitated by ether, decanted, and dried in vacuo to give 12 as an off-white powder (735 mg, ca 92% yield).

When macromonomer 15 is substituted for 11, the hyperbranched polymer 20 obtained is essentially the same as 12 but contains OH as the chain terminating group (A in the figure) instead of $NH_2$.

The hyperbranched polymers 5a, 5b, 8, 10, 12, 16, 17, 18, 19, and 20 have utility as adhesives, biomaterials, coatings, compatibilizers, components of blends, crosslinkers, viscosity modifiers, drug carriers, vectors for gene therapy, carriers for agrochemicals such as antifungal agents, slow release agents, biodegradable materials, imaging materials, resists for lithography, carriers for image contrast agents, components of medical imaging formulations and dispersants.

EXAMPLE XI

Preparation of 2-octyl-2-oxazoline

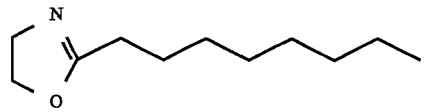

A mixture of octyl cyanide (75.0 g, 0.539 mol), anhydrous zinc acetate (2.47 g, 0.0134 mol) and 1-butanol (270 ml) was stirred at 120° C. under nitrogen. To this mixture was dropwisely added 2-hydroxyethyl amine (39.5 g, 0.647 mol) in 20 min., and the resulting mixture was stirred at 120° C. for 40 h. The resulting admixture was distilled under reduced pressure three times. The fraction at 75°–80° C./0.2 mm Hg was collected to give 2-octyl-2-oxazoline as a colorless liquid (46 g, 47% yield). The product was again distilled under reduced pressure from calcium hydride: 1H NMR (CDC13) delta 0.88 (5, J=6.6 Hz, 3H, CH3), 1.29 (m, 10H, CH2X8), 1.63 (t of t, J=6.6 and 6.9 Hz, 2H, CH2), 2.26 (t, J=7.2 Hz, 2H, CH2), 3.82 (t, J=9.6 Hz, 2H, CH2O), and 4.22 (t, J=9.6, 2H, CH2N).

Many variations will be obvious to those skilled in the art. Thus, the invention is defined by the claims.

What is claimed is:

1. Polyoxazolines having the structural formula:

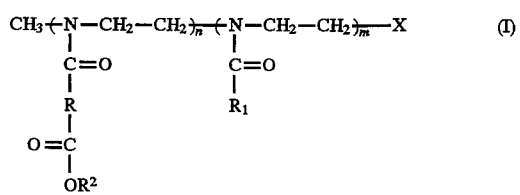

where X is $NH_2$ or OH, R is phenylene or alkylene containing 2 to 18 carbon atoms when X is $NH_2$, R is phenylene when X is OH, $R^2$ is $C_{1-4}$ alkyl, $R_1$ is selected from the group consisting of $C_{1-12}$ alkyl, vinyl, isopropylidene, pentafluoroethyl, phenyl, hydroxyphenyl which is optionally interrupted by up to 20 ethylene oxide groups, $C_{1-12}$-alkoxyphenyl which is optionally interrupted by up to 20 ethylene oxide groups and $-(CH_2CH_2-O-)_rCH_3$ in which r ranges from 1–20, n ranges from 2 to 50, and m ranges from 0 to 50, wherein $R_1$ is hydroxyphenyl which is optionally interrupted by up to 20 ethylene oxide groups only when X is $NH_2$.

2. Polyoxazoline as described in claim 1 wherein X is $NH_2$.

3. Polyoxazoline as described in claim 2 wherein R is phenylene, $R^2$ is $C_{1-4}$ alkyl, n ranges from 4 to 25 and m is 0.

4. Polyoxazoline as described in claim 2 wherein R is alkylene containing 2 to 18 carbon atoms, $R^2$ is $C_{1-4}$ alkyl, n ranges from 4 to 25 and m is 0.

5. Polyoxazoline as described in claim 4 wherein R is alkylene containing 4 carbon atoms.

6. Polyoxazoline as described in claim 2 wherein R is phenylene, $R^2$ is $C_{1-4}$ alkyl, n ranges from 4 to 25 and m ranges from 4 to 25, which is a block copolymer or a non block copolymer.

7. Polyoxazoline as described in claim 2 wherein R is alkylene containing 2 to 18 carbon atoms, $R^2$ is $C_{1-4}$ alkyl, n ranges from 4 to 25 and m ranges from 4 to 25, which is a block copolymer or a non block copolymer.

8. Polyoxazoline as described in claim 7 wherein R is alkylene containing 4 carbon atoms.

9. Polyoxazoline as described in claim 1 wherein X is OH.

10. Polyoxazoline as described in claim 1 wherein $R^2$ is methyl and $R_1$ is ethyl.

* * * * *